United States Patent [19]

Cosman

[11] Patent Number: 5,792,146

[45] Date of Patent: Aug. 11, 1998

[54] RECTILINEAR LINAC PHANTOM POINTER SYSTEM

[76] Inventor: Eric R. Cosman, 872 Concord Ave., Belmont, Mass. 02178

[21] Appl. No.: 623,662

[22] Filed: Mar. 28, 1996

Related U.S. Application Data

[63] Continuation of Ser. No. 398,624, Jul. 28, 1994, abandoned, which is a continuation of Ser. No. 979,480, Nov. 20, 1992, abandoned, which is a continuation of Ser. No. 595,205, Oct. 9, 1990, abandoned.

[51] Int. Cl.⁶ ............................................... A61B 19/00
[52] U.S. Cl. ............................................... 606/130; 606/1
[58] Field of Search ........................ 606/130, 1; 378/163, 378/164, 180

[56] References Cited

U.S. PATENT DOCUMENTS

| | | | |
|---|---|---|---|
| 3,073,310 | 1/1963 | Mocarski | 606/130 |
| 4,583,537 | 4/1986 | Derechinsky et al. | 606/130 |
| 4,722,336 | 2/1988 | Kim et al. | 606/130 |
| 4,750,487 | 6/1988 | Zanetti | 606/130 |
| 4,846,173 | 7/1989 | Davidson | 606/130 |
| 4,875,478 | 10/1989 | Chen | 606/130 |
| 5,027,818 | 7/1991 | Bova et al. | 606/130 X |
| 5,037,374 | 8/1991 | Carol | 606/130 X |
| 5,160,337 | 11/1992 | Cosman | 606/130 |

OTHER PUBLICATIONS

Winston and Lutz, "Linear Accelerator . . . Radiosurgery", Neurosurgery, vol. 22, No. 3, pp. 454–464, 1988.

*Primary Examiner*—Michael Peffley
*Attorney, Agent, or Firm*—Richard J. Birch

[57] ABSTRACT

This patent relates to instrumentation for confirming the position of a target, frequently in the head, at the isocenter of a linear accelerator or other beam delivery system. Typically, the anatomical target is determined by CT, NMR, angiographic, X-ray, or other imaging means. The position of the target and the coordinates of the target are referenced to a head fixation means. That head fixation means is subsequently attached to the beam delivery system, such as a linear accelerator (LINAC). To simulate the position of the target prior to putting the patient there, this rectilinear phantom pointer can be used. It has three coordinate slide scales on it that are orthogonal and are calibrated with distant scales. Moving these three scales positions a radiopaque marker to stand at the phantom point of the actual anatomical target. This enables direct confirmation of patient positioning and centering of the beam isocenter at the desired target.

5 Claims, 2 Drawing Sheets

RECTILINEAR LINAC PHANTOM POINTER SYSTEM

This application is a continuation of application Ser. No. 08/398,624 filed on Jul. 28, 1994, abandoned, which is a continuation of Ser. No. 07/979,480 filed on Nov. 20, 1992, abandoned which is a continuation of Ser. No. 07/595,205 filed on Oc. 9, 1990, abandoned.

BACKGROUND TO THE INVENTION

The use of linear accelerators (LINAC's) or other particle beams is now common for the treatment of intracranial arteriovenous malformations (AVM's) and tumors. The position of these anatomical targets is determined by various imaging means such as CT scan, MRI, angiography, or X-ray. Usually a head ring, or other patient fixation means, is clamped to the patient's head to provide a fixed coordinate reference base. Localizers are used during the scanning phase to determine the exact coordinates of the target. These coordinates are usually Cartesian or rectinlinear and specified as AP, Lateral, and Vertical, meaning the anterior-posterior direction, lateral direction, and vertical direction, as referenced to the patient's head and specifically to the head ring. The method of focal irradiation under such so-called stereotactic guidance is to now translate the patient's head to the focal point or isocenter of the LINAC or other accelerator or particle delivery system and then bombard the target while spreading out the beams over the hemisphere of the head. This produces intense radiation at the target, but spreads it out over intervening tissue. What is done is to translate the patient's head, and particularly the head ring which is attached to it, in the rectilinear AP, Lateral, and Vertical directions so that the target corresponds to the isocenter of the LINAC, for example. This is described in detail in the paper by Winston and Lutz where the use of the LINAC with the BRW Stereotactic System is detailed. Important in this process is confirming prior to putting the patient under beam that the target is correctly positioned. A LINAC phantom pointer has been used by Winston and Lutz for this purpose. The phantom pointer, as described in their article, is transferred from a rectilinear phantom base apparatus to the attachment means on the linear accelerator to simulate the positioning of the actual anatomical target. The phantom pointer has an adjustable rod system and a radiopaque ball or pointer at the tip of the rod so that if correctly positioned taking radiation beam shots from the LINAC, backed up by photographic emulsions, will demonstrate that the radiopaque ball is at the center of the collimation of the beam. The rectilinear phantom base mentioned above is a device which simulates the head ring on the patient and has a movable pointer, with rectilinear slide movements that can be positioned relative to the phantom ring so as to simulate the position of the target relative to the actual patient's head ring. The Winston-Lutz LINAC phantom pointer is now attached to the phantom base ring, and the adjustable rods are pointed to the phantom pointer rods so as to simulate the target position. The Winston-Lutz LINAC phantom pointer is now placed over onto the patient holding means on the LINAC so that if the patient translation means on the LINAC is adjusted properly, the anatomical target, and thus the simulated radiopaque pointer of the LINAC phantom pointer, shall be at the isocenter of the linear accelerator. If this is the case, then all of the beams of the LINAC should approach the radiopaque ball of the LINAC phantom pointer, and this will be demonstrated by taking test shots with X-ray films behind the phantom ball. The ball should then appear at the center of collimated cone of beam, as shown on the X-rays. This is the standard test method for checking the positioning of a target with a LINAC, and it has been used for several years.

A problem with the Winston-Lutz LINAC phantom pointer in that technique is that one requires a separate phantom base, and one is required to transfer the mechanical Winston-Lutz phantom pointer to the patient holding means on a LINAC. Not only does it require the separate phantom base, but in the process of transferral, several interfaces must be exactly precise so that the transfer position data will be accurate. Thus it would be desirable to eliminate the need for the separate phantom base and for the transfer process altogether. It is one of the objectives of the present invention to eliminate those steps and ancillary phantom apparatus. Another objective of the present invention is to eliminate inaccuracies associated with having a multiplicity of such devices. It is noteworthy that the phantom base coordinate slides may differ slightly from the theoretical coordinates axes associated with the patient holding means on the LINAC table or floor mount. If this is the case, then transfer of coordinate data from the phantom base could be inaccurate, once transferred to the LINAC. Thus, it is desirable to have a rectilinear coordinate system attached directly to the LINAC which has slide positions that are by definition along the orthogonal slide positions of the LINAC. This is achieved by the combined rectilinear phantom pointer as described in this invention, and thus an object of the invention is to assure greater accuracy of the coordinate representation of the phantom pointer. Yet another objective of the present invention is that the rectilinear phantom pointer can easily be digitized or encoded so that the coordinate positioning coordinates can be read out electronically, thus eliminating one possible human error factor in target simulation.

DESCRIPTION OF THE INVENTION

Figure 1:
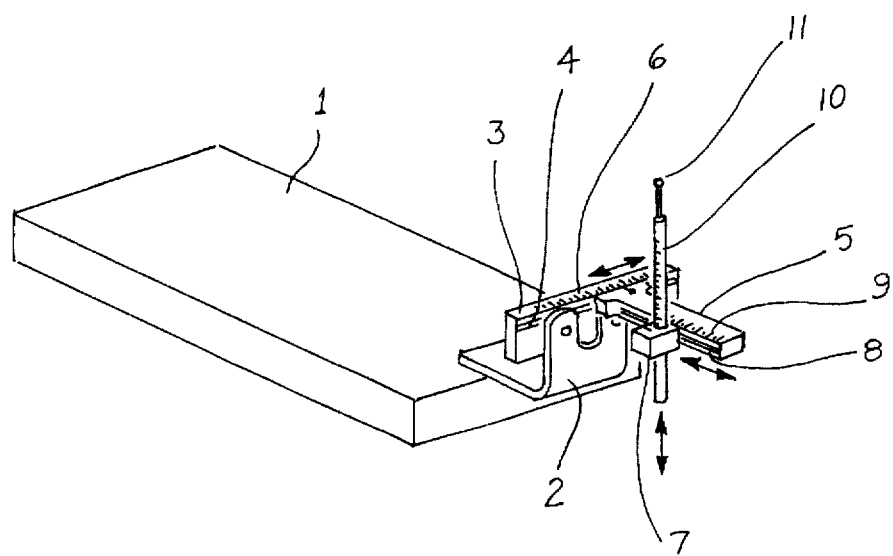
FIG. 1 shows an example of a rectilinear phantom pointer attached to a couch mount that would be used to support the patient on a LINAC. This is an embodiment of the present invention.
Figure 2:
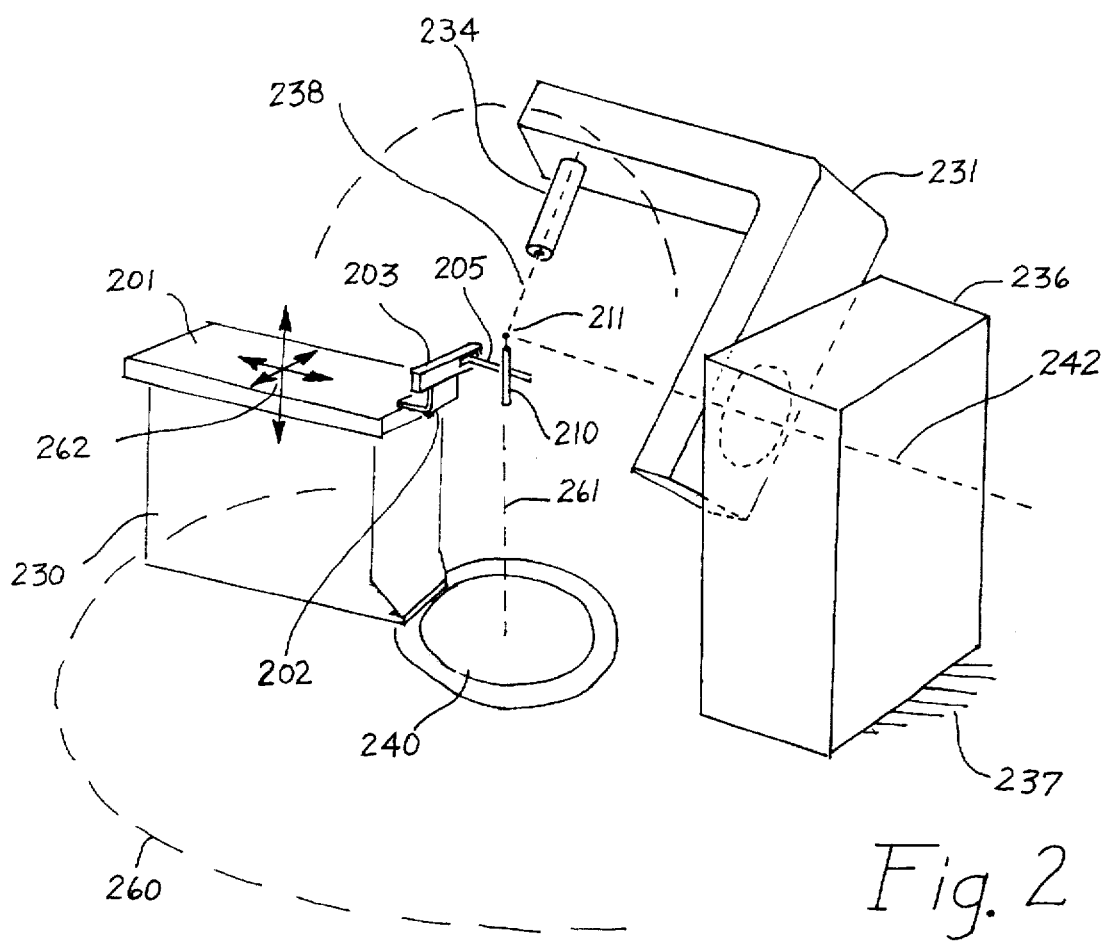
FIG. 2 shows the present invention, as well as the gantry and couch movements of the LINAC to orient it relative to the use on the LINAC.

FIG. 1 and FIG. 2 show an embodiment of the present invention as attached to a LINAC. What will be described here is illustrated in the figures as an attachment to a couch-mounted LINAC facility, meaning that the patient fixation means or holding means for the patient's head is attached to the LINAC couch. The couch could equally well have been replaced by an independent head holder attached to the floor bearing of the LINAC, which is commonly done and described in the paper by Winston and Lutz.

FIG. 1 and FIG. 2 show the patient couch, indicated as 1 in FIG. 1. The patient lies on that during the procedure of irradiation. The bracket 2 is attached to the couch 1 and can be used to hold the patient's head ring during radiation. To simulate the target position, we have shown the rectilinear phantom pointer in place on bracket 2. This consists of the horizontal element 3, which has a groove 4 in it. The element 5 slides laterally in that groove, and the scale 6 indicates the position in that lateral direction of the element 5 in groove 4. Element 5 similarly has a groove 8 in which element 7 slides to give the patient's vertical coordinate movements. Scale 9 on element 5 indicates the position of element 7 in the groove 8. The post 10 slides in a hole or groove in element 7, and its scale markings illustrate the position in 7, and thus the AP coordinate relative to the patient's head. On the end of element 7 is the radiopaque marker 11, which may be a ball or a point or other structure that can be visualized during the test shots with the radiation beam. Thus the marker 11 can be moved in rectilinear or Cartesian coordinate space; that is to say, three orthogonal linear coordinates by means of the three slides 10, 7, and 5. The millimeter markings on the slides just described can correspond to the stereotactic coordinate space, or the coordinate system, which has been defined relative to the patient head ring. Thus these coordinates correspond directly to the target position in the patient's head. Thus, by attaching this rectilinear phantom pointer onto the couch element 2, one is simulating the position of the anatomical target in the patient's head relative to the couch. The fact that you have quantitative Cartesian linear slides means that you do not have to transfer a phantom pointer, such as the Winston-Lutz phantom pointer, from the phantom base over to element 2 and thus incur all the inaccuracies that would entrain therefrom. Those inaccuracies have to do with any abnormalities or tolerance errors at all the interface positions of the Winston-Lutz LINAC phantom pointer to the standard phantom base and the element 2 of the patient holding means. By the means shown in FIG. 1, you essentially have a phantom base built into the rectilinear phantom pointer with its own metered coordinate axes, and it has only a single attachment to the bracket 2, thus eliminating the need for a separate phantom base and eliminating numerous possible interface errors.

FIG. 2 shows the positioning of this rectilinear phantom pointer on the LINAC. The LINAC has a gantry 231, which rotates about a horizontal axis 242. The gantry carries the beam collimator 231 from which a beam of photons, which is well collimated, passes to the target position illustrated as 211. In addition, the couch 201 rotates about a vertical axis 261 by means of the bearing 240. The rotating structure 230 has on top of it the couch 201, which has the capability of moving in the three orthogonal directions illustrated by the arrows 262, which correspond to the three principle axes of the stereotactic system referred to above as the AP, Lateral, and Vertical axes. Thus, the patient, when he lies on the couch, can be positioned and moved in these three orthogonal directions so that the anatomical target is at the intersection of the horizontal and vertical axes 242 and 261. At this point, all of the radiation is "piled up," and you get the most intense dose. The patient would typically have a head ring on him that would be placed in bracket 202. Bracket 202 in this case is holding the rectilinear phantom pointer, illustrated by the principle pieces 203, 205, and 210. On top of that vertical element 210 is a radiopaque ball which is located at the point 211, the isocenter of the LINAC. Typically, that rectilinear phantom pointer would be put into position to verify the proper couch translation positions, and then a test shot would be made under beam with photographic emulsions behind the ball so that it would appear as a round shadow at the center of the pencil of collimation of the beam.

Figure 3:
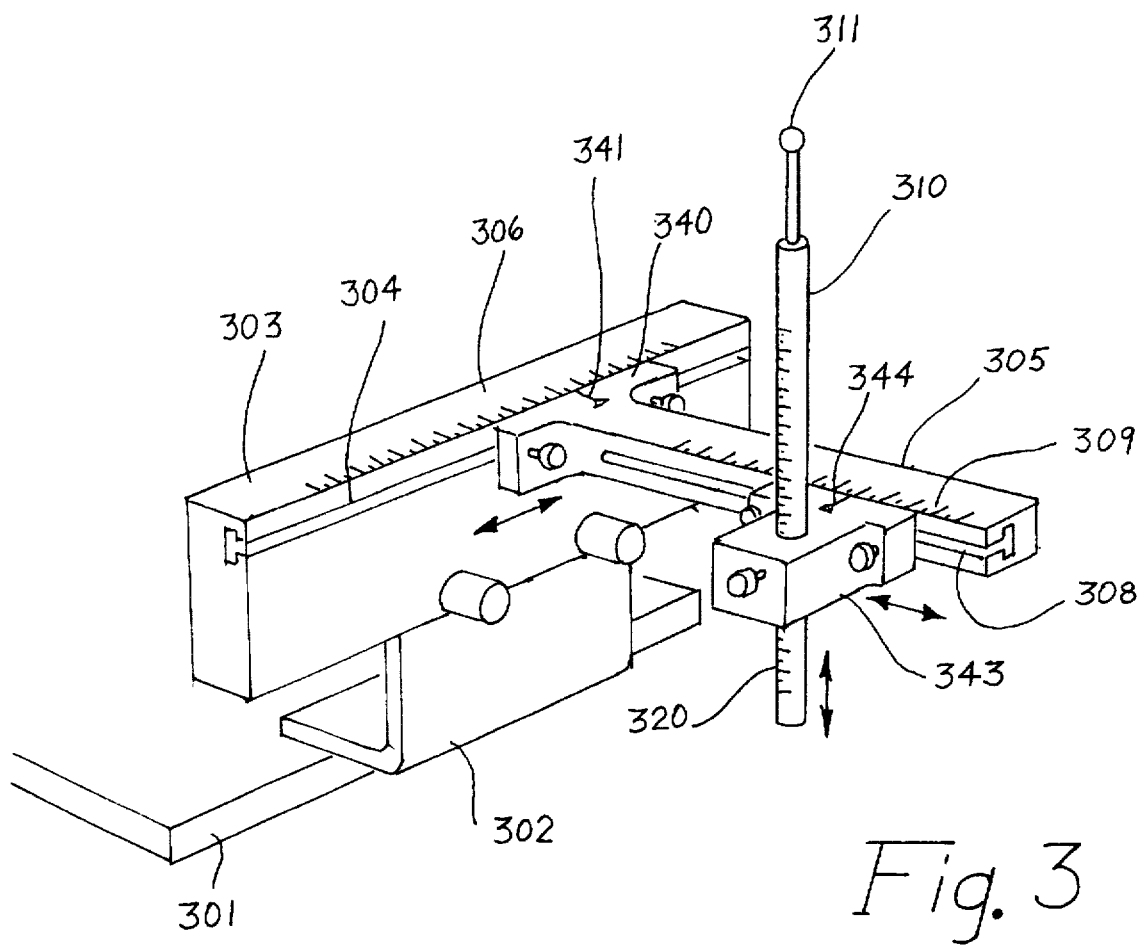
FIG. 3 shows a close-up view of the present invention in one embodiment detailing the rectilinear slides and illustrating the use of encoders to read out the coordinates electronically.

FIG. 3 shows a more detailed view of the apparatus in FIG. 1 and FIG. 2. It shows in expanded scale the end of the couch 301 with the right angle securing bracket 302. Onto 302 is the horizontal element 303, which has in it a groove 304 in which the slide element 340 slides. On 340 is an index mark 341, which is juxtaposed to the scale 306 so that the lateral position of 340 relative to element 303 can be determined by this reading. This scale can be directly in millimeters and in stereotactic coordinates as used for the patient. Base 340 connects to the element 305, which similarly has a scale 309 on it. It has a groove 308, which carries the slide element 343, and it has a corresponding index mark 344 juxtaposed to scale 309 so that one can determine its position in the patient's vertical direction. Finally, there is element 310, which passes in the hole in element 343 to give the patient's simulated AP position. It has a scale on it 320 so that one can determine the degree of anterior-posterior movement of the element 310. There are also illustrated various set screws that are not numbered to illustrate locks for these three orthogonal rectilinear motions. On top of element 310 is the radiopaque object illustrated as a ball 311.

The orthogonal movements illustrated in FIG. 3 could be encoded electronically or otherwise so that one would get a digital or analog readout of the position, rather than having to read the scales on the various elements shown. Thus the elements could have encoders, rack and pinion systems, or magnetic strips, etc. to accordingly read out these rectilinear coordinates, thus further reducing the possibility of errors that could be made by misreading of scales.

It is also possible to make other geometric arrangements of rectilinear slides than those illustrated in FIG. 3. Various types of travels, such as ball bushings on ground shafts, double shaft arrangements with low friction travel, V-groove travels, could all be envisaged by those skilled in the art. The radiopaque ball 311 in FIG. 3 could be replaced by a pointer or other structure to be identified on a radiographic or optical film. The base system 303 could be part of a simulated head ring or attachment that could accept a simulated head ring to perform other functions, such as putting on angiographic, reticule, diagonal rod, or laser light spatial index means that could further act as references relative to the position determined by the three rectilinear slide movements. Such an embodiment could be thought of in terms of a known commercial entity, the CRW Stereotactic System. For instance, the base 303 could be replaced by the equivalent of the CRW Head Ring, which is intended to be attached to bracket 302 when the patient is in place. Onto that head ring could be placed the base of the CRW Arc System, which has millimeter scales engraved on it for the AP and Lateral movements. The index pointed rod 310 with its ball 311 could then be placed on one of the AP or Lateral travels of the CRW base, thus achieving a vertical movement and achieving the radiographic target point, as illustrated by the embodiment in FIG. 3. All such variations and embodiments are anticipated by the present invention and would be included in the Claims. A significant difference between the design of the invention described in FIGS. 1, 2, and 3 and the previous Winston-Lutz LINAC phantom pointer is that the previous Winston-Lutz LINAC phantom pointer had an arbitrary analog pointing arm which was used in conjunction with a separate phantom base that had the rectilinear metric scales. Thus, the Winston-Lutz LINAC phantom pointer was not a self-contained, quantifiable phantom base plus phantom pointer, but only an analog transfer object. It had all the encumbrances and inaccuracies which were cited above, and these are eliminated by the present invention.

Having described the present invention, what I claim in U.S. Letters Patent are the following:

1. In combination, a linear accelerator, a patient holder and a rectilinear phantom pointer adapted to provide target localization testing on the linear accelerator, said rectilinear phantom pointer having:

a) three mechanically interconnected orthogonal translation elements which provide movement in three orthogonal directions, said three translation elements having scales on them to quantify the position of translation of said translation elements; and, b) a radiopaque marker means cooperatively connected to said three orthogonal translation elements for translation in space according to the translation of said three translation elements with said radiopaque marker means' position in space quantified by said scales;

an attachment mechanically connected to said translation elements and to said patient holder, said attachment releasably securing said three orthogonal translation elements with respect to said patient holder;

whereby said radiopaque marker means can be quantitatively positioned in space by said three translation means and said scales so that said radiopaque marker means can simulate the position of a physiologic target in a patient when said patient is held by said patient holder.

2. The combination of claim 1 wherein said radiopaque marker comprises a radiopaque ball.

3. The combination of claim 1 wherein said three orthogonal translation elements and said scales on said translation elements correspond to three orthogonal stereotactic axes defined relative to a patient by a stereotactic guidance means, and whereby an anatomical target of said patient, which has been determined stereotactically by said stereotactic guidance means, can be simulated by said radiopaque marker when said radiopaque marker is translated to the appropriate position by said translation elements, as indicated by said scales, whereby said radiopaque marker simulates the position of said anatomical target by means of film test shots of said the linear accelerator to confirm the position of said anatomical target by said radiopaque marker position.

4. The combination of claim 1 in which said three translation elements have readout means associated with each of the three translation elements for providing an output that corresponds to the measurements of said scales for each of said translation elements.

5. A method for target localization testing of the combination of a particle beam emitter and a patient holder, said method comprising the steps of:

(1) releasably attaching a rectilinear phantom pointer with respect to said patient holder, said rectilinear phantom pointer having (i) three mechanically interconnected orthogonal translation elements which provide movement in three orthogonal directions with each orthogonal translation element having a scale thereon that quantifies its translational position;

(ii) a radiopaque marker cooperatively connected to the three orthogonal translation elements so that the radiopaque marker can be translated in space according to the translation of the three orthogonal translation elements with the radiopaque marker's position in space quantified by the scales on said orthogonal translation elements;

(2) translating said radiopaque marker to a position corresponding to the three dimensional position of a stereotactically determined anatomical target of a patient by moving said orthogonal translation elements so that the radiopaque marker simulates the position of the anatomical target of the patient;

(3) confirming the position of the radiopaque marker by exposing a particle responsive media to the particles emitted by said particle beam emitter; and, (4) removing the rectilinear phantom pointer from said patient holder whereby the patient can be held by the patient holder so that the three dimensional position of the patient's anatomical target corresponds to the previously established three dimensional position of the radiopaque marker.

* * * * *